(12) United States Patent
Lecloux et al.

(10) Patent No.: US 7,517,594 B2
(45) Date of Patent: Apr. 14, 2009

(54) ELECTROLUMINESCENT PLATINUM COMPOUNDS AND DEVICES MADE WITH SUCH COMPOUNDS

(75) Inventors: Daniel David Lecloux, Wilmington, DE (US); Viacheslav A. Petrov, Hockessin, DE (US); Eric Maurice Smith, Hockessin, DE (US); Ying Wang, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 547 days.

(21) Appl. No.: 11/155,219

(22) Filed: Jun. 17, 2005

(65) Prior Publication Data
US 2005/0233234 A1 Oct. 20, 2005

Related U.S. Application Data

(62) Division of application No. 10/284,728, filed on Oct. 31, 2002, now Pat. No. 7,166,368.

(60) Provisional application No. 60/347,910, filed on Nov. 7, 2001.

(51) Int. Cl.
*H01L 51/00* (2006.01)
*H01L 51/54* (2006.01)
*C09K 11/06* (2006.01)

(52) U.S. Cl. .................. 428/690; 428/917; 313/504; 313/506; 257/40; 257/E51.044; 546/4; 546/10; 548/402; 549/3

(58) Field of Classification Search .................. None
See application file for complete search history.

(56) References Cited

U.S. PATENT DOCUMENTS

| | | | |
|---|---|---|---|
| 3,718,488 | A | 2/1973 | Trofimenko et al. |
| 5,552,678 | A | 9/1996 | Tang et al. |
| 6,303,238 | B1 | 10/2001 | Thompson et al. |
| 6,670,645 | B2 | 12/2003 | Grushin et al. |
| 7,320,833 | B2 * | 1/2008 | Dobbs et al. ............... 428/690 |
| 2001/0019782 | A1 | 9/2001 | Igarashi et al. |
| 2001/0053462 | A1 | 12/2001 | Mishima |
| 2002/0048689 | A1 * | 4/2002 | Igarashi et al. ............ 428/690 |
| 2002/0064681 | A1 | 5/2002 | Takiguchi et al. |
| 2002/0182441 | A1 * | 12/2002 | Lamansky et al. ......... 428/690 |
| 2003/0096138 | A1 | 5/2003 | Lecloux et al. |

FOREIGN PATENT DOCUMENTS

| | | |
|---|---|---|
| EP | 1 175 128 A2 | 1/2002 |
| EP | 1 191 614 A2 | 3/2002 |
| WO | WO 00/57676 A1 | 9/2000 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |
| WO | WO 03/063555 A1 | 7/2003 |

OTHER PUBLICATIONS

Balashev et al., "Crystal Structures and Spectroscopic Properties of trans-N,P-[Pt(ppy)(Pmor3)Cl]. . . phosphine]", Acta Chemica Scandinavica, vol. 50, 1996, pp. 1108-1115.*

Kulikova et al., "Synthesis, Spectra, and Luminescent . . . (phosphine)platinum(II) Complexes", Russian Journal of General Chemistry (Translation of Zhurnal Obshchei Khimii), vol. 69, No. 10, 1999, pp. 1521-1527.*

Lamansky Sergey et. al., Molecularly Doped Polymer Light Emitting Diodes Utilizing Phosphorescent Pt(II) and Ir(III) Dopants, Organic Electroncis, 2001, pp. 53-62, vol. 2, Elsevier Science B.V.

Djurovich, Peter I. et. al., Ir(III) Cyclometalated Complexes as Efficient Phosphorescent Emitters in Polymer Blend and Organic LEDs, Polymer Preprints, 2000, pp. 770-771, vol. 41 (1).

Chatani, Naoto et. al., Ru3(Co) 12-Catalyzed Reaction of Pyridylbenzenes With Carbon Monoxide and Olefins. Carbonylation at a C—H Bond in the Benzene Ring, J. Org. Chem., 1997, pp. 2604-2610, vol. 62, American Chemical Society.

Gosmini, Corinne et. al., Electosynthesis of Functionalized 2-Arylpyridines From Functionalized Aryl and Pyridine Halides Catalyzed by Nickel Bromide 2,2'-Bipyridine Complex, Tetrahedron Letters, 2000, pp. 5039-5042, vol. 41, Elsevier Science, Ltd.

Cacchi, Sandro et. al., The Palladium-Catalyzed Transfer Hydrogenation/Heterocyclization of B-(2-Aminophenyl-A,B-Ynones. An Approach to 2-Aryl and 2-Vinylquinolines, Synlett, 1999, pp. 401-404, No. 4, Thieme Stuttgart, New York.

Baldo, M. et. al., Very High-Efficiency Green Organic Light-Emitting Devices Based on Electrophosphorescence Applied Physics Letter, Jul. 5, 1999, pp. 4-6, 75(1) American Institute of Physics.

Baldo, M.A. et, al., High-Efficiency Fluorescent Organic Light-Emitting Devices Using a Phosphorescent Sensitizer, Nature, Feb. 17, 2000, pp. 750-753, vol. 403, MacMilan Magazines Ltd.

Wang, Yue et. al., (Hydroxyphenyl) Pyridine Derivative, Its Metal Complexes and Application as Electroluminescence Material Chemical Abstracts Service, Mar. 1, 2000, Database No. 133;315395.

Dedeian K. et, al., A New Synthetic Route to the Preparation of a Series of Strong Photoreducing Agents: Factris-Ortho-Metalated Complexes of Iridium(III) With Substituded 2-Phenylpyridines, Inorg. Chem., 1991, pp. 1685-1687, vol. 30 (8), American Chemical Society.

Baldo, M.A. et. al., Highly Efficient Phosphorescent Emission From Organic Electroluminescent Devices, Nature, Sep. 10, 1998, 151-154, vol. 395.

Lohse, Oliver et. al.,The Palladium Catalysed Suzuki Coupling of 2 and 4 Chloropyridines, Synlett, 1999, pp. 45-48, No. 1, Thieme Suttgart, New York.

Lamansky, Sergey et al., Highly Phosphorescent Bis-Cyclometalated Iridium Complexes, Synthesis, Photophysical Characterization and Use in Organic Light Emitting Diodes, J. Am. Chem. Soc,, 2001, pp. 4304-4312, vol. 128, American Chemical Society.

Lamansky, Sergey et. al., Synthesis and Characterization of Phosphorescent Cyclometalated Iridium Complexes, Inorg. Chem., 2001. pp. 1704-1711, vol. 40, American Chemical Society.

Abstract of Japanese PCT Publication WO02/44189 A1, Luminescent Element and Display, Jun. 6, 2002, Caon Kabushiki Kaisha.

Abstract of German PCT Publication WO96/03410, Hydrophilic Metal Complexes, Feb. 8, 1996, Boehringer Mannheim GMBH.

* cited by examiner

*Primary Examiner*—Marie R. Yamnitzky
(74) *Attorney, Agent, or Firm*—John H. Lamming

(57) ABSTRACT

The present invention is generally directed to electroluminescent Pt(II) complexes which have emission maxima across the visible spectrum, and devices that are made with the Pt(II) complexes.

9 Claims, 8 Drawing Sheets

(VII)

(VIII)

(IX)

(X)

Q = B(OH)$_2$ or MgBr (5-1)
 (5-9)
 (5-2)
 (5-10)
 (5-3)
 (5-11)
 (5-4)
 (5-12)
 (5-5)
 (5-13)
 (5-6)
 (5-14)
 (5-7)
 (5-15)
 (5-8)
 (5-16)

Eq. (2)

Eq. (3)

Eq. (4)

ELECTROLUMINESCENT PLATINUM COMPOUNDS AND DEVICES MADE WITH SUCH COMPOUNDS

This application is a division of U.S. application Ser. No. 10/284,728, filed Oct. 31, 2002, now U.S. Pat. No. 7,166,368, which claims priority to U.S. Provisional Application No. 60/347,910, filed Nov. 07, 2001.

BACKGROUND OF THE INVENTION

1. Field of the Invention

This invention relates to electroluminescent complexes of platinum(II) which have emission spectra across the visible spectrum. It also relates to electronic devices in which the active layer includes an electroluminescent Pt(II) complex.

2. Description of the Related Art

Organic electronic devices that emit light, such as light-emitting diodes that make up displays, are present in many different kinds of electronic equipment. In all such devices, an organic light-emitting layer is sandwiched between two electrical contact layers. At least one of the electrical contact layers is light-transmitting so that light can pass through the electrical contact layer. The organic layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8-hydroxyquinolate with trivalent metal ions, particularly aluminum, have been extensively used as electroluminescent components, as has been disclosed in, for example, Tang et al., U.S. Pat. No. 5,552,678.

Electroluminescent devices with an light-emitting layer of polymer doped with organometallic complexes of platinum have been disclosed by Burrows and Thompson in published PCT applications WO 00/57676.

However, there is a continuing need for efficient electroluminescent compounds which emit light across the visible spectrum.

SUMMARY OF THE INVENTION

The present invention is directed to a metal complex having Formula I or Formula II:

$$PtL^1L^2 \quad (I)$$

$$PtL^1L^3L^4 \quad (II)$$

Where:
in Formula I:
 $L^2$ is a monoanionic bidentate ligand;
in Formula II:
 $L^3$ is a monodentate ligand; and
 $L^4$ is a monodentate phosphine ligand;
in Formulae I and II:
 $L^1$ is selected from Formula III, shown in FIG. 1, and Formula VII, shown in FIG. 2, where:
in Formulae III and VII:
 $E^1$ through $E^4$ are the same or different at each occurrence and are $CR^2$ or N;

$R^2$ is the same or different at each occurrence and is selected from H, D, $C_n(H+F)_{2n+1}$, F, $OC_n(H+F)_{2n+1}$, $OCF_2Y$, $SR^3$, and $N(R^3)_2$, or adjacent $R^2$ groups can join to form a 5- or 6-membered ring;
$R^3$ is H, $C_nH_{2n+1}$;
Y is H, Cl, or Br;
n is an integer from 1 through 12;
in Formula III:
A is N or $SR^3$;
$R^1$ is the same or different at each occurrence and is selected from D, $C_n(H+F)_{2n+1}$, F, $OC_n(H+F)_{2n+1}$, $OCF_2Y$, $SR^3$, and $N(R^3)_2$, or adjacent R groups can join to form a 5- or 6-membered ring;
α is 0, 1 or 2; and
in Formula VII:
$R^4$ through $R^7$ are the same or different at each occurrence and are selected from H, D, $C_n(H+F)_{2n+1}$, F, $OC_n(H+F)_{2n+1}$, $OCF_2Y$, $SR^3$, and $N(R^3)_2$, or adjacent R groups can join to form a 5- or 6-membered ring.

In another embodiment, the present invention is directed to an organic electronic device having at least one active layer comprising the above metal complex, or combinations of the above metal complexes.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The letter "L" is used to designate a ligand having a nominal (−1) charge formed from the neutral parent compound, "HL", by the loss of a hydrogen ion. The term "complex", when used as a noun, is intended to mean a compound having at least one metallic ion and at least one ligand. The term "β-dicarbonyl" is intended to mean a neutral compound in which two ketone groups are present, separated by a CHR group. The term "β-enolate" is intended to mean the anionic form of the β-dicarbonyl in which the H from the CHR group between the two carbonyl groups has been abstracted. The term "group" is intended to mean a part of a compound, such as a substituent in an organic compound or a ligand in a complex. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. In addition, the IUPAC numbering system is used throughout, where the groups from the Periodic Table are numbered from left to right as 1 through 18 (CRC Handbook of Chemistry and Physics, 81$^{st}$ Edition, 2000). In the Formulae and Equations, the letters A, E, L, R, Q, Y and Z are used to designate atoms or groups which are defined within. All other letters are used to designate conventional atomic symbols. The term "(H+F)" is intended to mean all combinations of hydrogen and fluorine, including completely hydrogenated, partially fluorinated or perfluorinated substituents. By "emission maximum" is meant the wavelength, in nanometers, at which the maximum intensity of electroluminescence is obtained. Electroluminescence is generally measured in a diode structure, in which the material to be tested is sandwiched between two electrical contact layers and a voltage is applied. The light intensity and wavelength can be measured, for example, by a photodiode and a spectrograph, respectively.

DETAILED DESCRIPTION OF THE PREFERRED EMBODIMENTS

The metal complexes of the invention have Formula I or Formula II, given above, and are referred to as cyclometallated complexes. The platinum is in the +2 oxidation state and is tetracoordinate. The complex in Formula I is a cyclometallated complex with an additional monoanionic bidentate ligand, $L^2$. The complex in Formula II is a cyclometallated complex with two additional monodentate ligands, $L^3$ and $L^4$. The preferred cyclometallated complexes are neutral and non-ionic, and can be sublimed intact. Thin films of these materials obtained via vacuum deposition exhibit good to excellent electroluminescent properties.

The complexes of the invention have emission spectra with maxima ranging from the blue region through the red region. The color of emission can be tuned by selection of the appropriate ligands, as discussed below.

Figure 1:
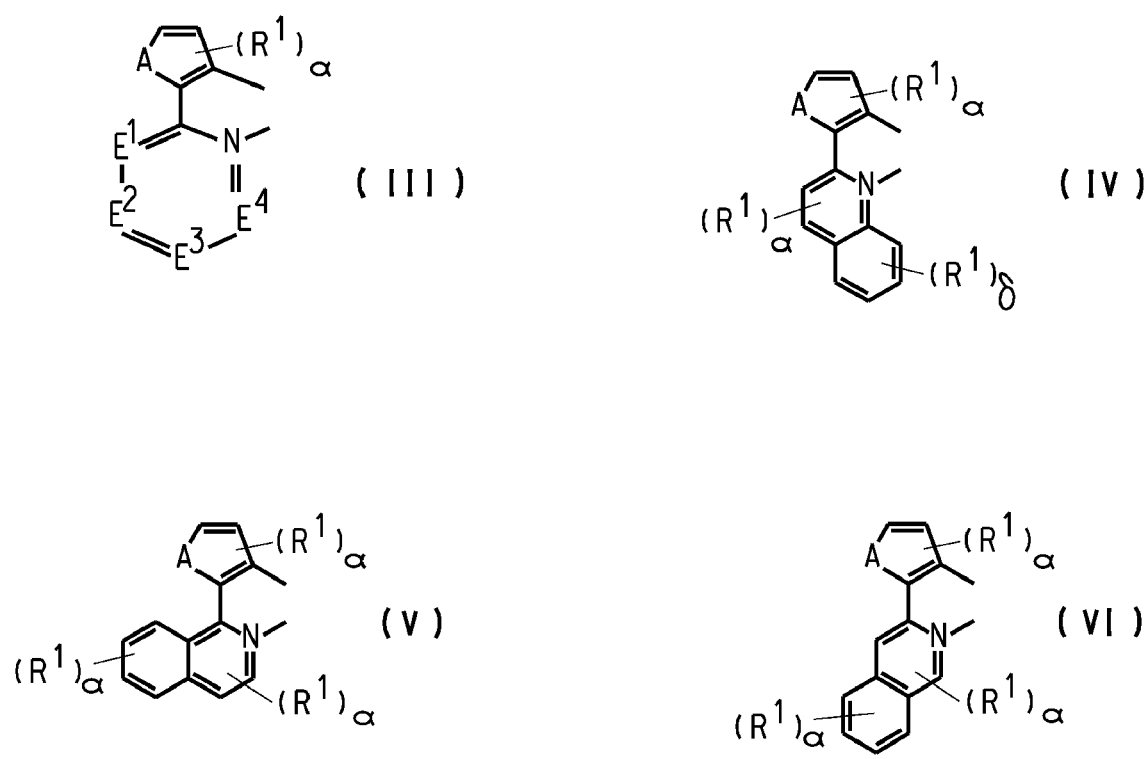
FIG. 1 shows Formulae III through VII for the ligand $L^1$ in the metal complex of the invention.

Ligand $L^1$ having Formula III, shown in FIG. 1, is derived from a parent compound in which a thienyl group (when A is S) or pyrrolyl group (when A is $NR^3$) is bonded to a 6-membered ring having at least one nitrogen. It is preferred that α is 0. When A is $NR^3$, it is preferred that $R^3$ is $CH_3$.

When all E are $CR^2$, and the $R^2$ groups are individual substituents that are not joined to form a ring, the ligands are derived from thienyl- and pyrrolyl-pyridine parent compounds. It is preferred that there is at least one deuterium or fluorine-containing substituent on the pyridine ring, more preferably at the $E^1$ and $E^3$ positions. Preferred fluorine-containing substituents are F and $CF_3$.

Other types of ligands having the general structure of Formula III, have quinoline or isoquinoline groups in place of pyridine, as shown in Formulae IV through VI of FIG. 1. Ligand $L^1$ having Formula IV, shown in FIG. 1, is derived from a thienyl- or a pyrrolyl-quinoline parent compound. Ligand $L^1$ having Formula V or Formula VI, shown in FIG. 1, is derived from a thienyl- or a pyrrolyl-isoquinoline parent compound. In these figures δ is 0 or an integer from 1 through 4, $R^1$, α, and A are as defined above in Formula III. It is preferred that at least one substituent on the quinoline or isoquinoline ring is selected from D, $C_n(F)_{2n+1}$, F, $OC_n(F)_{2n+1}$, and $OCF_2Y$.

Figure 2:
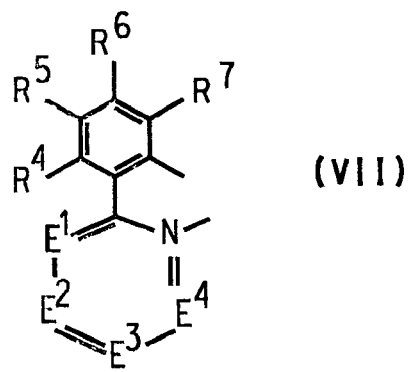
FIG. 2 shows Formulae VII through X for the ligand $L^1$ in the metal complex of the invention.
Figure 2:
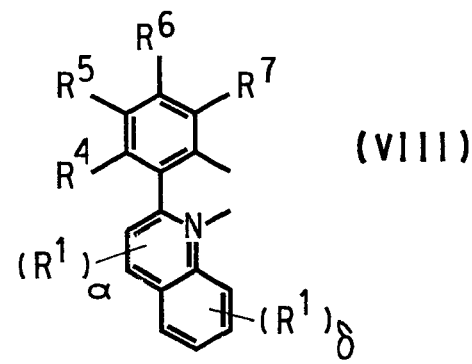
Figure 2:
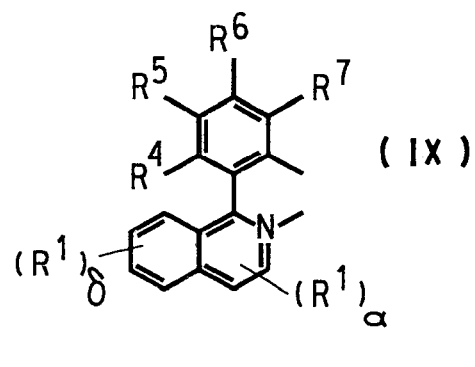
Figure 2:
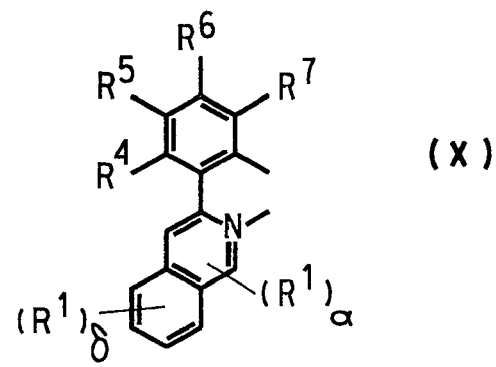

Ligand $L^1$ having Formula VII, shown in FIG. 2, is derived from a parent compound in which a phenyl group is bonded to a 6-membered ring having at least one nitrogen.

When all E are $CR^2$, and the $R^2$ groups are individual substituents that are not joined to form a ring, the ligands are derived from phenyl-pyridine parent compounds. It is preferred that there is at least one deuterium or fluorine-containing substituent on the ligand, more preferably at the $E^1$ and $E^3$ positions. Preferred fluorine-containing substituents are F and $CF_3$.

Other types of ligands having the general structure of Formula VII, have quinoline or isoquinoline groups in place of pyridine, as shown in Formulae VIII through X, of FIG. 2. Ligand $L^1$ having Formula VIII, shown in FIG. 2, is derived from a phenyl-quinoline parent compound. Ligand $L^1$ having Formula IX or Formula X, shown in FIG. 2, is derived from a phenyl-isoquinoline parent compound. In these figures δ is 0 or an integer from 1 through 4, and $R^1$ and α are as defined above in Formula III, and $R^4$ through $R^7$ are as defined above in Formula VII. It is preferred that at least one substituent on the ligand is selected from D, $C_n(F)_{2n+1}$, F, $OC_n(F)_{2n+1}$, and $OCF_2Y$.

Figure 4:
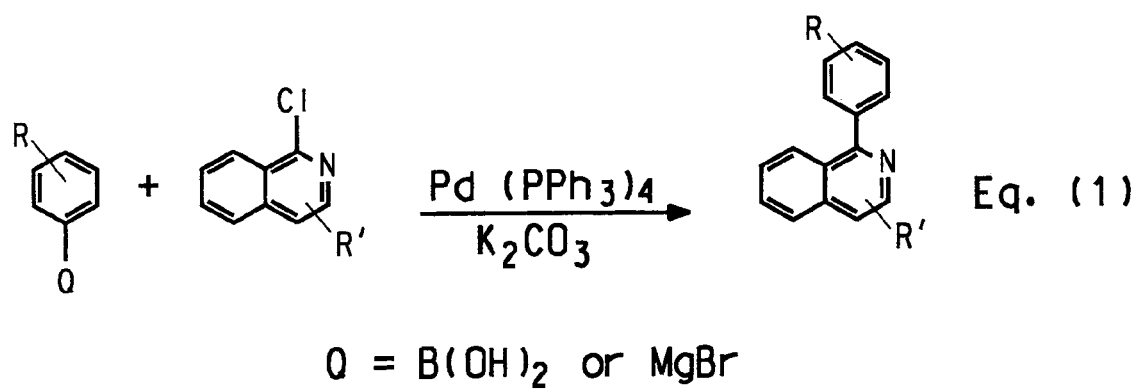
FIG. 4 shows Equation (1) for synthesis of the parent ligand compounds, $HL^1$, useful in the invention.

The parent ligand compounds, $HL^1$, can generally be prepared by standard palladium-catalyzed Suzuki or Kumada cross-coupling of the corresponding heterocyclic aryl chloride with an organoboronic acid or organomagnesium reagent, as described in, for example, O. Lohse, P. Thevenin, E. Waldvogel *Synlett,* 1999, 45-48. This reaction is illustrated for a phenyl-isoquinoline, where R and R' represent substituents, in Equation (1) in FIG. 4. The partially or fully deuterated ligand parent compounds can generally be prepared by the same coupling methods using deuterated components. The deuterated components are often commercially available, or can be made by known synthetic methods.

The $L^2$ ligand is a monoanionic bidentate ligand. In general these ligands have N, O, P, or S as coordinating atoms and form 5- or 6-membered rings when coordinated to the platinum. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).

Figure 3:
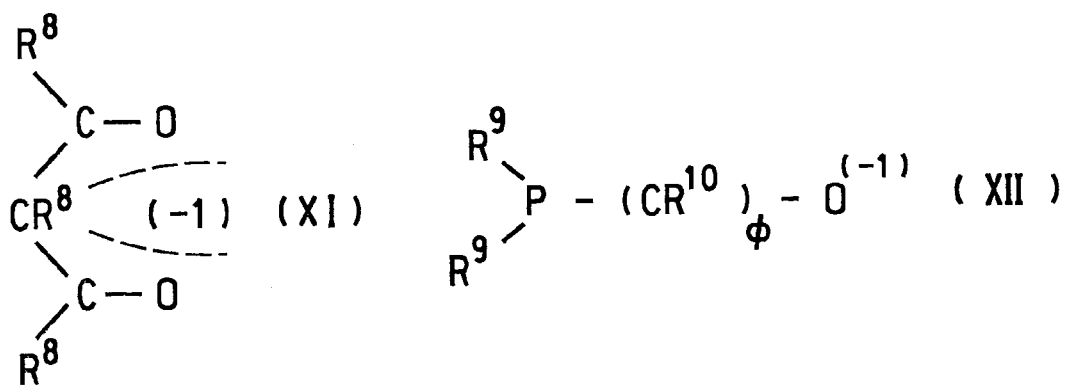
FIG. 3 shows Formula XI for the β-enolate ligand and Formula XII for the phosphinoalkoxide ligand useful in the invention.

The β-enolate ligands generally have Formula XI shown in FIG. 3, where $R^8$ is the same or different at each occurrence. The $R^8$ groups can be hydrogen, halogen, substituted or unsubstituted alkyl, aryl, alkylaryl or heterocyclic groups. Adjacent $R^8$ groups can be joined to form five- and six-membered rings, which can be substituted. Preferred $R^8$ groups are selected from H, F, $C_n(H+F)_{2n+1}$, $—C_6H_5$, $—C_4H_3S$, and $—C_4H_3O$, where n is an integer from 1 through 12, preferably from 1 to 6.

Examples of suitable β-enolate ligands include the compounds listed below. The abbreviation for the β-enolate form is given below in brackets.

2,4-pentanedionate [acac]
1,3-diphenyl-1,3-propanedionate [DI]
2,2,6,6-tetramethyl-3,5-heptanedionate [TMH]
4,4,4-trifluoro-1-(2-thienyl)-1,3-butanedionate [TTFA]
7,7-dimethyl-1,1,1,2,2,3,3-heptafluoro-4,6-octanedionate [FOD]
1,1,1,3,5,5,5-heptafluoro-2,4-pentanedionate [F7acac]
1,1,1,5,5,5-hexaflouro-2,4-pentanedionate [F6acac]

1-phenyl-3-methyl-4-i-butyryl-pyrazolinonate [FMBP]

The β-dicarbonyl parent compounds, are generally available commercially. The parent compound 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step. This compound should be stored and reacted under anyhydrous conditions as it is susceptible to hydrolysis.

The hydroxyquinolinate ligands can be substituted with groups such as alkyl or alkoxy groups which may be partially or fully fluorinated. Examples of suitable hydroxyquinolinate ligands include (with abbreviation provided in brackets):

8-hydroxyquinolinate [8hq]
2-methyl-8-hydroxyquinolinate [Me-8hq]
10-hydroxybenzoquinolinate [10-hbq]

The parent hydroxyquinoline compounds are generally available commercially.

Phosphino alkoxide ligands generally have Formula XII, shown in FIG. 3, where $R^9$ can be the same or different at each occurrence and is selected from $C_n(H+F)_{2n+1}$ and $C_6(H+F)_5$,
$R^{15}$ can be the same or different at each occurrence and is selected from H and $C_n(H+F)_{2n+1}$, and
φ is 2 or 3.

Examples of suitable phosphino alkoxide ligands include (with abbreviation provided in brackets):

3-(diphenylphosphino)-1-oxypropane [dppO]
1,1-bis(trifluoromethyl)-2-(diphenylphosphino)-ethoxide [tfmdpeO]

Some of the parent phosphino alkanol compounds are available commercially, or can be prepared using known procedures, such as, for example, the procedure reported for tfmdpeO in *Inorg. Chem.* 1985, v. 24, p. 3680.

Figure 5:
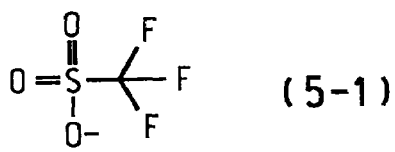
FIG. 5 shows the formulae of $L^3$ ligands useful in the invention.
Figure 5:
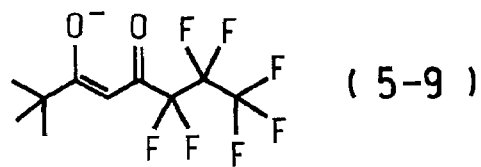
Figure 5:
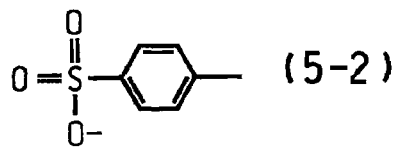
Figure 5:
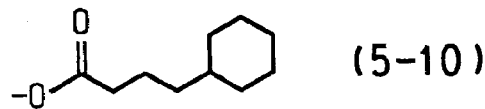
Figure 5:
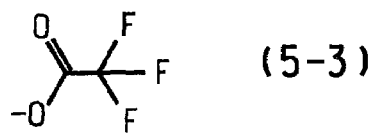
Figure 5:
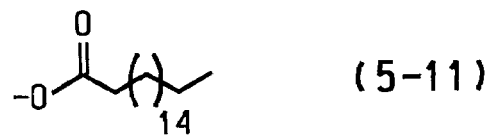
Figure 5:
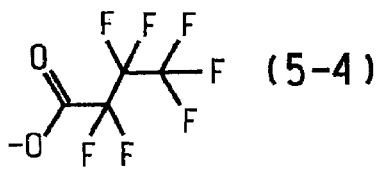
Figure 5:
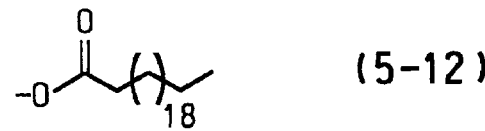
Figure 5:
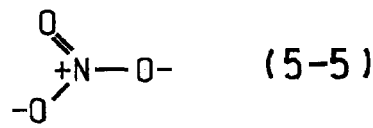
Figure 5:
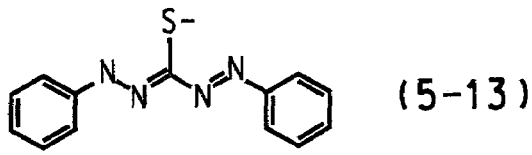
Figure 5:
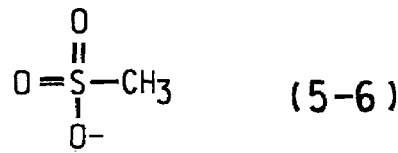
Figure 5:
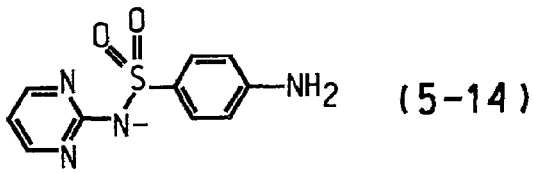
Figure 5:
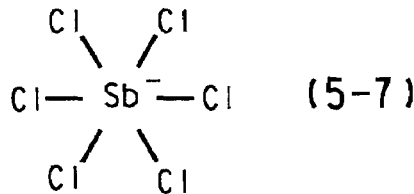
Figure 5:
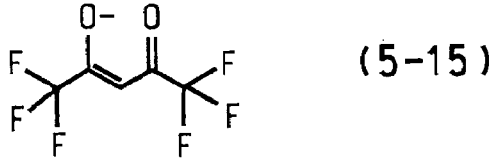
Figure 5:
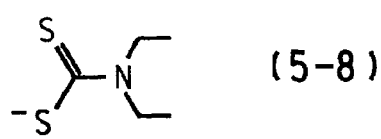
Figure 5:

The $L^3$ ligand is a monodentate ligand. Preferably this ligand is monoanionic. Such ligands can have O or S as coordinating atoms, with coordinating groups such as alkoxide, carboxylate, thiocarboxylate, dithiocarboxylate, sulfonate, thiolate, carbamate, dithiocarbamate, thiocarbazone anions, sulfonamide anions, and the like. In some cases, ligands such as β-enolates can act as monodentate ligands. The $L^3$ ligand can also be a coordinating anion such as halide, nitrate, sulfate, hexahaloantimonate, and the like. Examples of suitable $L^3$ ligands are shown in FIG. 5.

The $L^3$ ligands are generally available commercially.

Figure 6A:
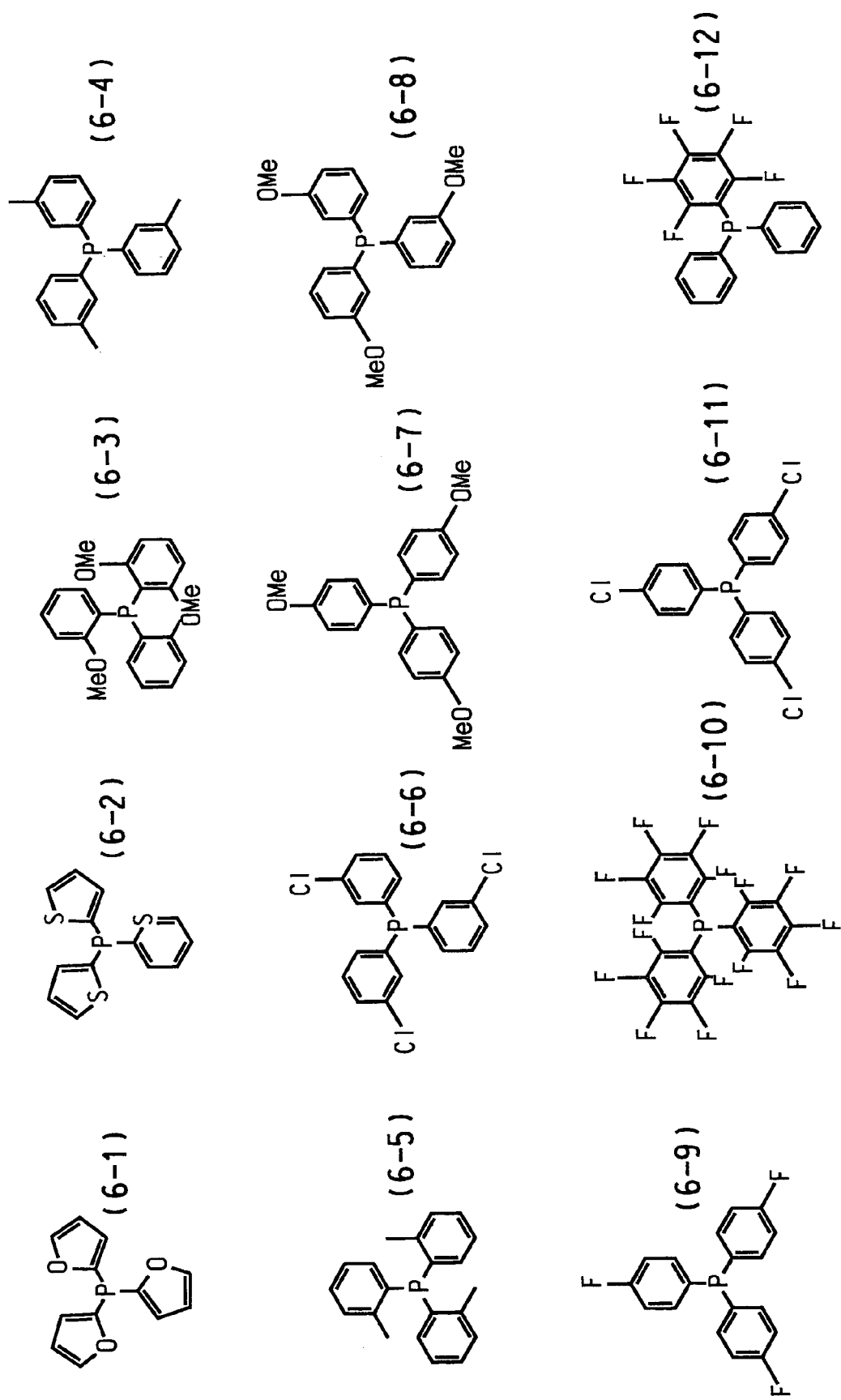
FIGS. 6A and 6B show the formulae of $L^4$ ligands useful in the invention.
Figure 6B:
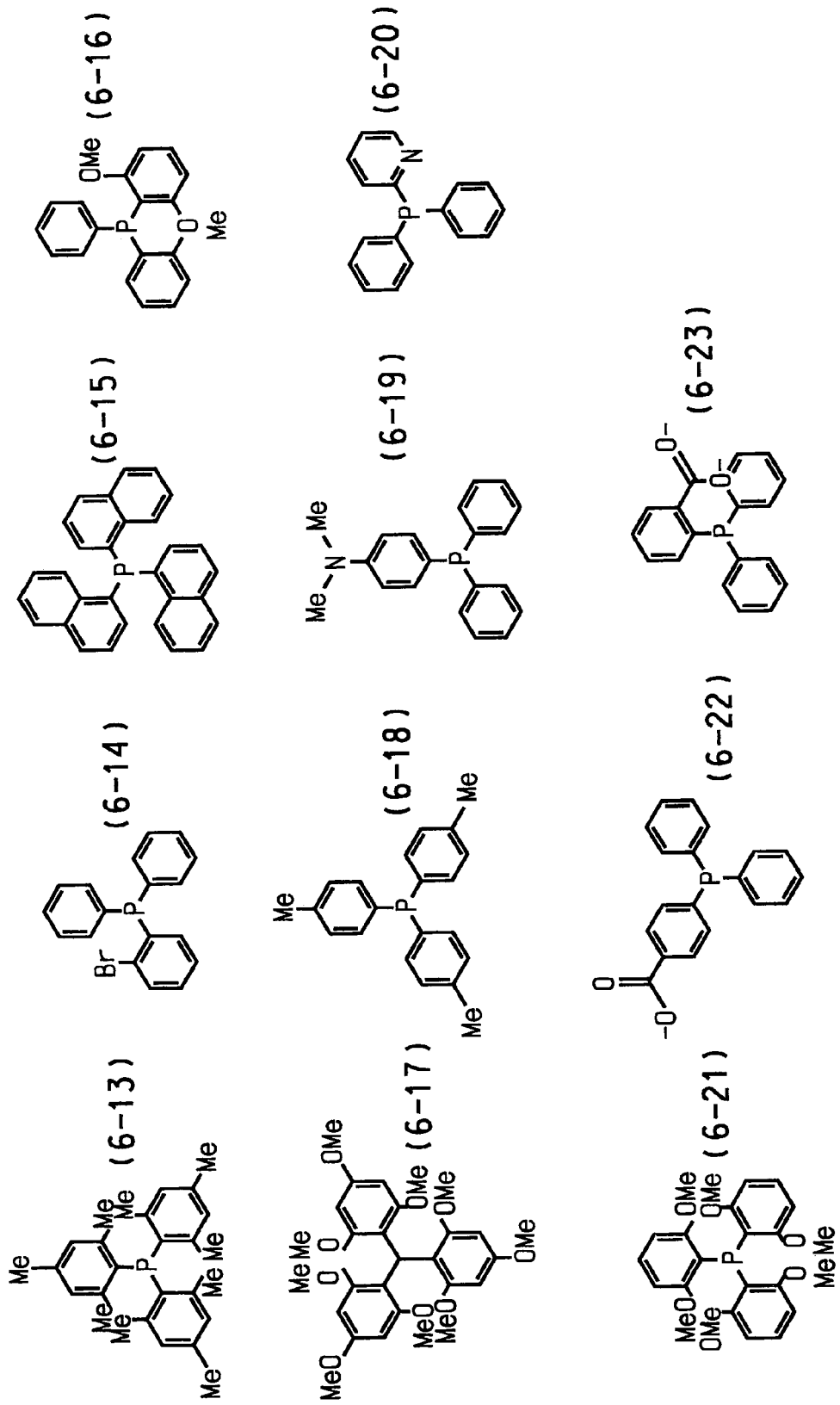

The $L^4$ ligand is a monodentatephosphine ligand. Preferably, this ligand in non-ionic. The phosphine ligands can have Formula XIII $$PAr_3 \tag{XIII}$$

where Ar represents an aryl or heteroaryl group. The Ar group can be unsubstituted or substituted with alkyl, heteroalkyl, aryl, heteroaryl, halide, carboxyl, sulfoxyl, or amino groups. Examples of suitable $L^4$ ligands are shown in FIGS. 6A and 6B, where the "Me" is used to designate a methyl group in Formulae 6-3, 6-8, 6-8 of FIG. 6A and Formulae 6-13, 6-16, 6-17, 6-18, 6-19, and 6-21 of FIG. 6B. The $L^4$ phosphine ligands are generally available commercially.

The color of luminescence of the complexes of Formulae I and II, is largely determined by the choice of ligands, $L^1$, $L^2$, $L^3$ and $L^4$. In general, the color is shifted to longer wavelengths ("red-shifted") when $L^1$ has Formula III. The color is shifted to shorter wavelengths ("blue-shifted") when $L^1$ has Formula VII. The complex is also blue-shifted when the nitrogen-containing ring of the ligand has at least one substituent bonded through a heteroatom having non-bonding pi electrons, most preferably oxygen, or at least one substitutent capable of sigma electron donation, such as alkyl groups, and preferably methyl. However, exceptions to these general guidelines do occur.

The luminescence efficiency of the complexes may be improved by using $L^1$ ligands in which some or all of the hydrogens have been replaced with deuterium.

Figure 7:
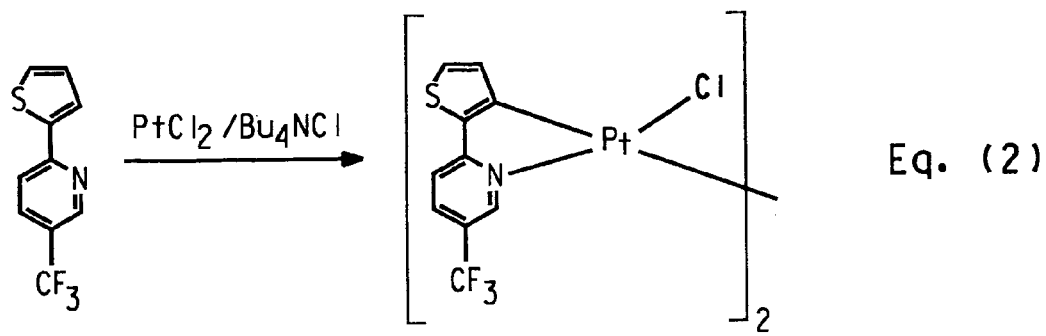
FIG. 7 shows Equations (2) and (3) for forming complexes of Formula I, useful in the invention.
Figure 7:
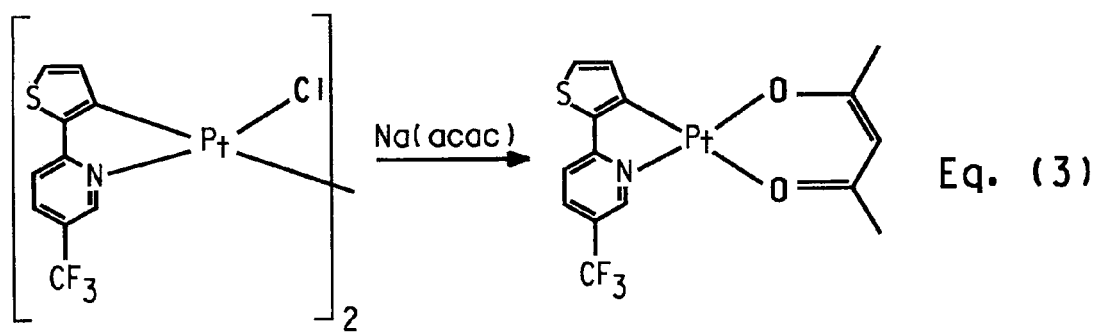

Complexes of Formula I are generally prepared from metal chloride salts by first forming the bridged chloride dimer. This reaction is illustrated for a thienyl-pyridine ligand in Equation (2), shown in FIG. 7. Complexes of Formula I are then formed by adding a salt of the parent ligand compound, such as $NaL^2$, to the bridged chloride dimer. This reaction is illustrated using the sodium salt of a β-enolate ligand in Equation (3) in FIG. 7. The salts of the parent ligand compounds can be made by any conventional methods, such as by the addition of sodium hydride to $HL^2$ in an inert solvent.

Examples of metal complexes of the invention having Formula I are given in Table 1 below. At each occurrence, α and delta are zero.

TABLE 1

| Complex | $L^1$ Formula | A | Substituents | $L^2$ |
|---|---|---|---|---|
| 1-a | III | N—$CH_3$ | $E^1 = E^3 = E^4 = CH$<br>$E^1 = CCF_3$ | acac |
| 1-b | IX | — | none | acac |
| 1-c | IX | — | $R^6 = $ t-butyl | acac |
| 1-d | IX | — | $R^5 = OCH_3$ | acac |
| 1-e | IX | — | $R^6 = CF_3$ | acac |
| 1-f | IX | — | $R^6 = F$ | acac |
| 1-g | VII | — | $E^1 = E^2 = E^4 = CH$<br>$E^3 = CCH_3$<br>$R^5 = CF_3$<br>$R^7 = CF_3$ | TMH |
| 1-h | VII | — | $E^1 = E^3 = E^4 = CH$<br>$E^2 = COCH_3$<br>$R^5 = CF_3$ | tfmdpeO |
| 1-i | VII | — | $E^1 = E^3 = E^4 = CH$<br>$E^2 = COCH_3$<br>$R^4 = F$<br>$R^6 = F$ | TMH |
| 1-j | VII | — | $E^1 = E^2 = E^4 = CH$<br>$E^3 = CCH_3$<br>$R^4 = F$<br>$R^6 = F$ | tfmdpeO |
| 1-k | VII | — | $E^1 = E^3 = E^4 = CH$<br>$E^2 = COC(CH_3)_3$<br>$R^4 = F$<br>$R^6 = F$ | TMH |
| 1-l | VII | — | $E^1 = E^2 = E^4 = CH$<br>$E^3 = CCH_3$<br>$R^4 = F$<br>$R^6 = F$ | TMH |
| 1-m | VII | — | $E^1 = E^2 = E^4 = CH$<br>$E^3 = CCH_3$<br>$R^5 = CF_3$ | TMH |

Figure 8:
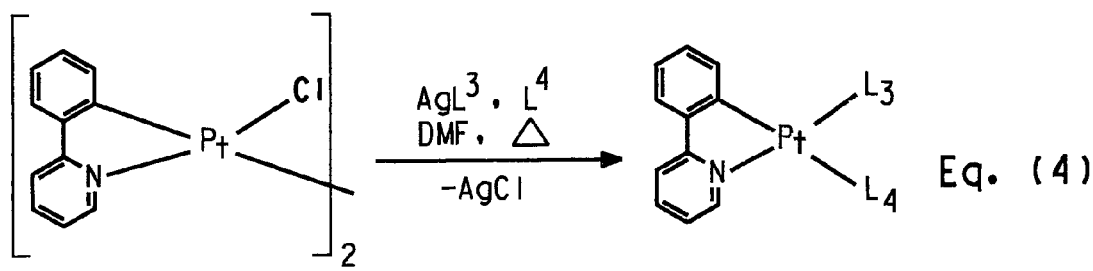
FIG. 8 shows Equation (4) for forming complexes of Formula II, useful in the invention.

Complexes of Formula II are also generally prepared by first forming the bridged chloride dimer. To the dimer is then added the other two ligands. Preferably, $L^3$ is monoanionic and is added as the silver salt, $AgL^3$. $L^4$ is added as the neutral ligand or, in the case of anionic ligands, as a salt such as $NaL^4$. The preferred reaction is illustrated for a bridged chloride dimer having a phenyl-pyridine ligand in Equation (4), shown in FIG. 8.

A combinatorial library of complexes having Formula II was prepared where $L^1$ was selected from one of the ligands in Table 2 below, $L^3$ was selected from the ligands shown in FIG. 5, and $L^4$ was selected from the ligands shown in FIGS. 6A and 6B.

TABLE 2

| Ligand | L$^1$ Formula | A | α | Substituents |
|---|---|---|---|---|
| 2-a | III | S | 0 | E$^1$ = E$^2$ = E$^4$ = CH<br>E$^3$ = CCF$_3$ |
| 2-b | III | N—CH$_3$ | 0 | E$^1$ = E$^2$ = E$^4$ = CH<br>E$^3$ = CCF$_3$ |
| 2-c | VII | — | — | E$^1$ = E$^3$ = E$^4$ = CH<br>E$^2$ = COCH$_3$<br>R$^5$ = CF$_3$ |
| 2-d | VII | — | — | E$^1$ = E$^2$ = E$^4$ = CH<br>E$^3$ = COCH$_3$<br>R$^5$ = CF$_3$ |
| 2-e | VII | — | — | E$^1$ = E$^3$ = E$^4$ = CH<br>E$^2$ = CCH$_3$<br>R$^4$ = F<br>R$^6$ = F |
| 2-f | VII | — | — | E$^1$ = E$^3$ = E$^4$ = CH<br>E$^2$ = COCH$_3$<br>R$^4$ = F<br>R$^6$ = F |

Most of the complexes having ligand 2-a or 2-b have red to red-orange luminescence. Most of the complexes having ligands 2-c, 2-d, 2-e, or 2-f have blue or blue-green luminescence.

Electronic Device

Figure 9:
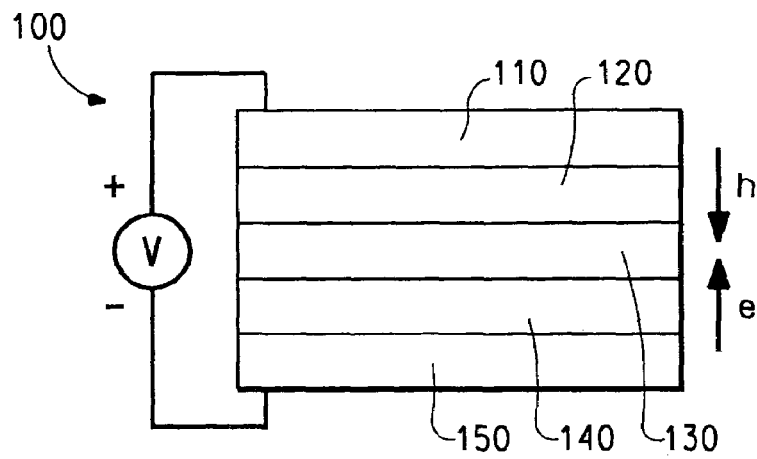
FIG. 9 is a schematic diagram of a light-emitting device (LED).

The present invention also relates to an electronic device comprising at least one photoactive layer positioned between two electrical contact layers, wherein the at least one photoactive layer of the device includes the complex of the invention. As shown in FIG. 9, a typical device 100 has an anode layer 110 and a cathode layer 150 and electroactive layers 120, 130 and optionally 140 between the anode 110 and cathode 150. Adjacent to the anode is a hole injection/transport layer 120. Adjacent to the cathode is an optional layer 140 comprising an electron transport material. Between the hole injection/transport layer 120 and the cathode (or optional electron transport layer) is the photoactive layer 130. Layers 120, 130, and 140 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The complexes of the invention are particularly useful as the active material in the emitting layer of an OLED, or as electron transport material in layer 140. Preferably the platinum complexes of the invention are used as the light-emitting material in diodes. When used in layer 130, it has been found that the complexes of the invention do not need to be in a solid matrix diluent in order to be effective. A layer that is greater than 20% by weight metal complex, based on the total weight of the layer, up to substantially 100% by weight metal complex, can be used as the emitting layer. By "substantially 100%" it is meant that the metal complex is the only material in the layer, with the possible exception of impurities and adventitious byproducts from the process to form the layer. Additional materials can be present in the emitting layer with the metal complex. For example, a fluorescent dye may be present to alter the color of emission. A diluent may also be added. Preferably, the diluent facilitates charge transport in the layer. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the metal complex is generally present in a small amount, usually less than 20% by weight, preferably less than 10% by weight, based on the total weight of the layer.

One type of diluent which is useful with the platinum metal complexes of the invention, is a conjugated polymer in which the triplet excited state of the polymer is at a higher energy level than the triplet excited state of the platinum complex. Examples of suitable conjugated polymers include polyarylenevinylenes, polyfluorenes, polyoxadiazoles, polyanilines, polythiophenes, polypyridines, polyphenylenes, copolymers thereof, and combinations thereof. The conjugated polymer can be a copolymer having non-conjugated portions of, for example, acrylic, methacrylic, or vinyl, monomeric units. Particularly useful are homopolymers and copolymers of fluorene and substituted fluorenes.

In some cases the metal complexes of the invention may be present in more than one isomeric form, or mixtures of different complexes may be present. It will be understood that in the above discussion of OLEDs, the term "the metal complex" is intended to encompass mixtures of complexes and/or isomers.

The device generally also includes a support (not shown) which can be adjacent to the anode or the cathode. Most frequently, the support is adjacent the anode. The support can be flexible or rigid, organic or inorganic. Generally, glass or flexible organic films are used as a support. The anode 110 is an electrode that is particularly efficient for injecting or collecting positive charge carriers. The anode is preferably made of materials containing a metal, mixed metal, alloy, metal oxide or mixed-metal oxide. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymers," *Nature* vol. 357, pp 477-479 (11 Jun. 1992).

The anode layer 110 is usually applied by a physical vapor deposition process or spin-cast process. The term "physical vapor deposition" refers to various deposition approaches carried out in vacuo. Thus, for example, physical vapor deposition includes all forms of sputtering, including ion beam sputtering, as well as all forms of vapor deposition such as e-beam evaporation and resistance evaporation. A specific form of physical vapor deposition which is useful is rf magnetron sputtering.

There is generally a hole transport layer 120 adjacent the anode. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules, in addition to TPD and MPMP mentioned above, are: 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino)benzaldehyde diphenylhydrazone (DEH); triphenylamine (TPA); 1-phenyl-3-[p-(diethylamino)styryl]-5-[p-(diethylamino)phenyl]pyrazoline (PPR or DEASP); 1,2-transbis(9H-carbazol-9-yl)cyclobutane (DCZB); N,N, N',N'-tetrakis(4-methylphenyl)-(1,1'-biphenyl)-4,4'-diamine (TTB); and porphyrinic compounds, such as copper phthalocyanine. Commonly used hole transporting polymers are polyvinylcarbazole, (phenylmethyl)polysilane, poly(3,4-ethylendioxythiophene) (PEDOT), and polyaniline. It is also possible to obtain hole transporting polymers by doping hole transporting molecules such as those mentioned above into polymers such as polystyrene and polycarbonate.

Optional layer 140 can function both to facilitate electron transport, and also serve as a buffer layer or anti-quenching layer to prevent quenching reactions at layer interfaces. Preferably, this layer promotes electron mobility and reduces quenching reactions. Examples of electron transport materials for optional layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

The cathode 150 is an electrode that is particularly efficient for injecting or collecting electrons or negative charge carriers. The cathode can be any metal or nonmetal having a lower work function than the first electrical contact layer (in this case, an anode). Materials for the second electrical contact layer can be selected from alkali metals of Group 1 (e.g., Li, Cs), the Group 2 (alkaline earth) metals, the Group 12 metals, the lanthanides, and the actinides. Materials such as aluminum, indium, calcium, barium, samarium and magnesium, as well as combinations, can be used.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole transport layer 120, 50-2500 Å, preferably 200-2000 Å; light-emitting layer 130, 10-1000 Å, preferably 100-800 Å; optional electron transport layer 140, 50-1000 Å, preferably 100-800 Å; cathode 150, 200-10,000 Å, preferably 300-5000 Å. The location of the electron-hole recombination zone in the device, and thus the emission spectrum of the device, is affected by the relative thickness of each layer. For examples, when an emitter, such as $Alq_3$ is used as the electron transport layer, the electron-hole recombination zone can be in the $Alq_3$ layer. The emission would then be that of $Alq_3$, and not the desired sharp lanthanide emission. Thus the thickness of the electron-transport layer must be chosen so that the electron-hole recombination zone is in the light-emitting layer. The desired ratio of layer thicknesses will depend on the exact nature of the materials used.

It is understood that the efficiency of the devices of the invention made with metal complexes, can be further improved by optimizing the other layers in the device. For example, more efficient cathodes such as Ca, Ba, Mg/Ag, or LiF/Al can be used. Shaped substrates and novel hole transport materials that result in a reduction in operating voltage or increase quantum efficiency are also applicable. Additional layers can also be added to tailor the energy levels of the various layers and facilitate electroluminescence.

The complexes of the invention often are phosphorescent and photoluminescent and may be useful in other applications. For example, the complexes may be used as oxygen sensitive indicators, as phosphorescent indicators in bioassays, and as catalysts.

EXAMPLES

The following examples illustrate certain features and advantages of the present invention. They are intended to be illustrative of the invention, but not limiting. All percentages are mole percents, unless otherwise indicated.

Example 1

This example illustrates the preparation of the parent ligand compound 2-(2,4-difluorophenyl)-4-methoxypyridine.

2-Chloro-4-methoxypyridine (Lancaster Synthesis Inc., 3.50 g, 24.4 mmol), 2,4-difluorophenylboronic acid (Aldrich Chemical Co., 3.85 g, 24.4 mmol), potassium carbonate (EM Science, 6.74 g, 48.8 mol), tetrakistriphenylphosphine palladium(0) (Aldrich Chemical Co., 400 mg, 0.346 mmol), dimethoxyethane (Aldrich, 50 mL), and water (50 mL) were allowed to stir at reflux under nitrogen for 15 hours. Then the organic component was separated, and the aqueous fraction was extracted with 3×25 mL of diethyl ether. The combined organic fractions were dried with sodium sulfate and evaporated to dryness. The resulting crude oil was purified by silica gel flash chromatography with hexanes/ethyl acetate (6:1) as the eluting solvent, to afford the desired product as a colorless oil, >95% pure by 1H NMR. Isolated yield=3.8 g (70%). $^1$H NMR ($CDCl_3$, 296 K, 300 MHz): δ 8.52 (1H, d, J=5.9 Hz), 7.99 (1H, m), 7.27 (1H, dd, J=2.1 and 2.0 Hz), 6.98 (1H, m), 6.89 (1H, m), 6.82 (1H, d, J=2.4 Hz), 3.89 (3H, s) ppm. $^{19}$F NMR ($CDCl_3$, 296 K, 282 MHz) δ=−109.05 (1F, dd, $J_{F-F}$=11 Hz and $J_{F-H}$=18 Hz), −112.80 (1F, brs) ppm.

Example 2

This example illustrates the formation of the bridged chloride dimer, [PtCl{2-(2,4-difluorophenyl)-4-methoxy-pyridine}]$_2$.

2-(2,4-Difluorophenyl)-4-methoxy-pyridine from Example 1 (1.50 g, 6.79 mmol), platinum(II) chloride (Strem Chemicals, 1.641 g, 6.17 mmol), anhydrous tetrabutylammonium chloride (Aldrich Chemical Co., 171 mg, 0.617 mmol), and chlorobenzene (Aldrich) were allowed to reflux under nitrogen for 15 hours, after which time the resulting precipitated product was isolated by filtration, washed with methanol, and dried in vacuo, to afford the desired product as an off-white solid. Isolated yield=2.31 g (75%). $^1$H NMR (DMSO-d6, 296 K, 300 MHz): δ 9.32 (1H, d, J=7.0 Hz), 8.01 (1H, dd, J=10.8 and 2.4 Hz), 7.50 (1H, dd, J=3.0 and 2.9 Hz), 7.18 (1H, dd, J=6.9 and 2.7 Hz), 7.05 (1H, m), 3.99 (3H, s) ppm. $^{19}$F NMR (DMSO-d6, 296 K, 282 MHz) δ=−106.79 (1F, d, $J_{F-F}$=11 Hz), −110.16 (1F, d, $J_{F-F}$=11 Hz) ppm.

Example 3

This example illustrates the formation of Pt(TMH){2-(2,4-difluoro-phenyl)4-methoxypyridine}, compound 1-i.

[PtCl{2-(2,4-difluorophenyl)4-methoxypyridine}]$_2$ from Example 2 (200 mg, 0.22 mmol), 2,2,6,6-tetramethyl-3,5-heptanedione, sodium salt (prepared from 2,2,6,6-tetramethyl-3,5-heptanedione, Aldrich Chemical Co., and sodium hydride, Aldrich; 120 mg, 0.56 mmol), and 2-ethoxyethanol (Aldrich, 20 mL) were allowed to stir at 120° C. for 45 minutes. Then the volatile components were removed in vacuo, and the resulting residue was redissolved in $CD_2Cl_2$ and passed through a pad of silica gel with $CD_2Cl_2$ as the eluting solvent. The blue-luminescent fraction (Rf=1.0) was collected and evaporated to dryness, to afford the desired product as a cream-colored solid. Isolated yield=212 mg (80%). $^1$H NMR ($CD_2Cl_2$, 296 K, 300 MHz): δ 8.76 (1H, d, J=6.8 Hz), 7.51 (1H, dd, J=2.7 and 2.6 Hz), 7.08 (1H, dd, J=8.7 and 2.3 Hz), 6.58 (1H, m), 5.85 (1H, s), 3.95 (3H, s), 1.27 (18H, s) ppm. $^{19}$F NMR ($CD_2Cl_2$, 296 K, 282 MHz) δ=−108.26 (1F, d, $J_{F-F}$=11 Hz), −113.36 (1F, d, $J_{F-F}$=11 Hz) ppm.

Compounds 1-a through 1-h, and 1-j through 1-m were prepared in an analogous manner to Examples 1-3.

Example 4

This example illustrates the formation of OLEDs using the platinum complexes of the invention.

Thin film OLED devices including a hole transport layer (HT layer), electroluminescent layer (EL layer) and at least one electron transport layer (ET layer) were fabricated by the thermal evaporation technique. An Edward Auto 306 evaporator with oil diffusion pump was used. The base vacuum for all of the thin film deposition was in the range of $10^{-6}$ torr. The deposition chamber was capable of depositing five different films without the need to break up the vacuum.

An indium tin oxide (ITO) coated glass substrate was used, having an ITO layer of about 1000-2000 Å. The substrate was first patterned by etching away the unwanted ITO area with 1N HCl solution, to form a first electrode pattern. Polyimide tape was used as the mask. The patterned ITO substrates were then cleaned ultrasonically in aqueous detergent solution. The substrates were then rinsed with distilled water, followed by isopropanol, and then degreased in toluene vapor for ~3 hours. Alternatively, patterned ITO from Thin Film Devices, Inc was used. These ITO's are based on Corning 1737 glass coated with 1400 Å ITO coating, with sheet resistance of 30 ohms/square and 80% light transmission.

The cleaned, patterned ITO substrate was then loaded into the vacuum chamber and the chamber was pumped down to $10^{-6}$ torr. The substrate was then further cleaned using an oxygen plasma for about 5-10 minutes. After cleaning, multiple layers of thin films were then deposited sequentially onto the substrate by thermal evaporation. Finally, patterned metal electrodes of Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

A summary of the device layers and thicknesses is given in Table 3. In all cases the anode was ITO as discussed above.

TABLE 3

| Sample | HT layer Thickness, Å | EL layer thickness, Å | ET layer thickness, Å | Cathode thickness, Å |
|---|---|---|---|---|
| 1 | MPMP 511 | Compound 1-a 412 | DPA 408 | Al 737 |
| 2 | MPMP 507 | Compound 1-b 421 | DPA 407 | Al 725 |
| 3 | MPMP 507 | Compound 1-c 419 | DPA 415 | Al 738 |
| 4 | MPMP 534 | Compound 1-d 420 | DPA 405 | Al 729 |
| 5 | MPMP 616 | Compound 1-e 404 | DPA 406 | Al 730 |
| 6 | MPMP 521 | Compound 1-f 430 | DPA 401 | Al 728 |
| 7 | MPMP 518 | Compound 1-g 407 | DPA 418 | Al 727 |
| 8 | MPMP 532 | Compound 1-h 570 | DPA 412 | Al 600 |
| 9 | MPMP 528 | Compound 1-i 418 | DPA 404 | Al 736 |
| 10 | MPMP 514 | Compound 1-j 483 | DPA 416 | Al 727 |
| 11 | MPMP 519 | Compound 1-k 423 | DPA 403 | Al 721 |
| 12 | MPMP 525 | Compound 1-l 411 | DPA 412 | Al 752 |
| 13 | MPMP 550 | Compound 1-m 406 | DPA 409 | Al 918 |

Figure 10:
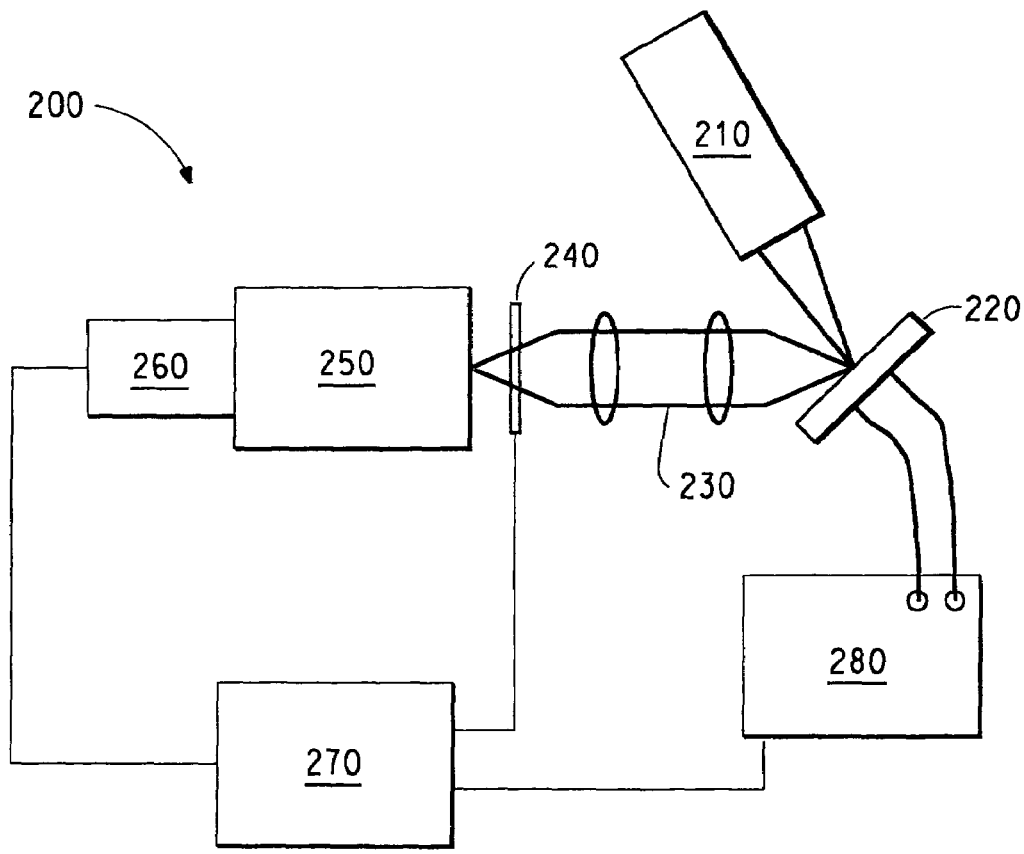
FIG. 10 is a schematic diagram of an LED testing apparatus.

DPA = 4,7-diphenyl-1,10-phenanthroline
ET = electron transport
EL = electroluminescence
HT = hole transport
MPMP = bis[4-(N,N-diethylamino)-2-methylphenyl](4-methylphenyl)methane The OLED samples were characterized by measuring their (1) current-voltage (I-V) curves, (2) electroluminescence radiance versus voltage, and (3) electroluminescence spectra versus voltage. The apparatus used, 200, is shown in FIG. 10. The I-V curves of an OLED sample, 220, were measured with a Keithley Source-Measurement Unit Model 237, 280. The electroluminescence radiance (in the unit of $Cd/m^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in Cd/A.

The results are given in Table 4 below.

TABLE 4

| | Electroluminescent Properties of Platinum Compounds | | |
|---|---|---|---|
| Sample | Peak Radiance, $Cd/m^2$ | Peak efficiency, Cd/A | Approximate Peak Wavelengths, nm |
| 1 | 8 at 19 V | 0.15 | 620 |

TABLE 4-continued

Electroluminescent Properties of Platinum Compounds

| Sample | Peak Radiance, Cd/m² | Peak efficiency, Cd/A | Approximate Peak Wavelengths, nm |
|---|---|---|---|
| 2 | 0.02 at 15 V | | |
| 3 | 30 at 19 V | 0.6 | 600 and 640 |
| 4 | 80 at 20 V | 0.38 | 640 and 690 |
| 5 | 25 at 20 V | 0.3 | 600 and 640 |
| 6 | 120 at 19 V | 1.7 | 590 and 640 |
| 7 | 16 at 20 V | 0.4 | 540 |
| 8 | 60 at 21 V | 4 | 475 and 505 |
| 9 | 130 at 23 V | 4 | 458 and 489 |
| 10 | 80 at 20 V | 7 | 476 and 508 |
| 11 | 0.2 at 23 V | 0.035 | |
| 12 | 90 at 19 V | 4.5 | 473 and 507 |
| 13 | 700 at 22 V | 9 | 474 and 507 |

Example 5

Prophetic

This example illustrates the formation of OLED's using a red-emissive Pt material of this invention in a poly(fluorene) polymer matrix. The resulting blend is used as the active red-emissive layer in an OLED. The platinum complex, Pt(acac){1-(5-t-butyl-phenyl)-isoquinoline}, compound 1-c in Table 1, will be prepared as described in Example 3. The polyfluorene will be prepared as described in Yamamoto, Progress in Polymer Science, Vol. 17, p 1153 (1992), where the dihalo, preferably dibromo, derivatives of the monomeric units are reacted with a stoichiometric amount of a zerovalent nickel compound, such as bis(1,5-cyclooctadiene)nickel(0).

The organic film components in this example will all be solution processed. Device assembly will be as follows: ITO/glass substrate (Applied Films) will be patterned (device active area=entire 3 cm²) and cleaned as directed in Example 4. The substrate will be further cleaned by placing in a 300 W plasma oven for 15 min. A poly(ethylenedioxythiophene)-poly(styrenesufonic acid) (PEDOT-PSSA, Bayer Corp.) buffer layer (i.e. hole transport/injection layer) will be spin-coated to a thickness of 90 nm. The film will be dried on a hotplate at 200° C. for 3 min. The substrate will then be transferred to a nitrogen-filled glovebox, at which point a solution of a poly(fluorene) polymer, [Pt(acac){1-(5-t-butyl-phenyl)-isoquinoline}] (1.6 μmol), and anhydrous toluene (7.5 mL) will be spin coated on the substrate to a thickness of 70 nm. The substrate will then be transferred to a high vacuum chamber, where Ba (3.5 nm) followed by Al (400 nm) will be thermally deposited at 2.0×10⁻⁶ torr. The resulting OLED device will be sealed from air by gluing a glass slide on top of the cathode with the use of a UV-curable epoxy resin.

The device will be fully characterized by acquiring current-voltage, luminance-voltage, luminance-current, efficiency-voltage, and efficiency-current profiles. This will be accomplished with the use of a computer-driven (Labview software) Keithley Source-Measurement Unit and a photodiode, the latter which will integrate light output over the entire 3 cm² device active area.

What is claimed is:

1. An active layer comprising at least one compound having Formula II:

PtL¹L³L⁴ (II)

where:

L¹ has a formula selected from Formula IV

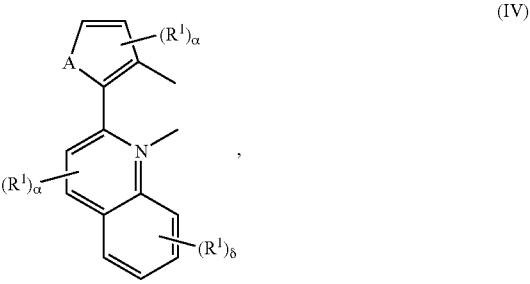

Formula V

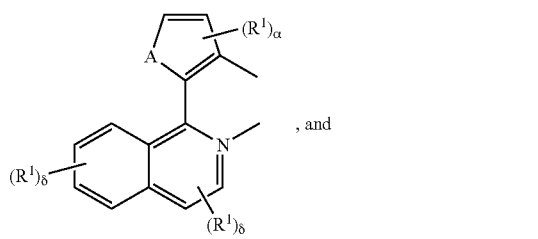

Formula VI

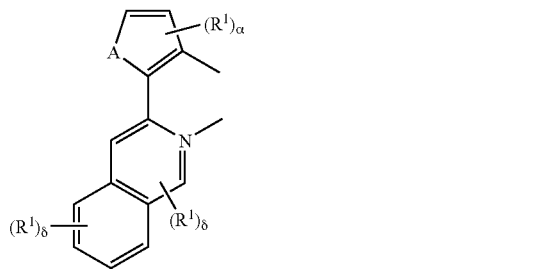

L³ is a monodentate ligand; and
L⁴ is a monodentate phosphine ligand;
A is S or NR³;
R¹ is the same or different at each occurrence and is selected from D, $C_n(H+F)_{2n+1}$, F, $OC_n(H+F)_{2n+1}$, $OCF_2Y$, $SR^3$, and $N(R^3)_2$, or adjacent R groups can join to form a 5- or 6-membered ring;
R³ is H, $C_nH_{2n+1}$;
Y is H, Cl, or Br;
n is an integer from 1 through 12;
α is 0, 1 or 2; and
δ is 0 or an integer from 1 through 4, provided that, where the active layer contains less than 20% by weight of the at least one compound, a diluent is also present.

2. The active layer of claim 1 wherein α is 0, and there is at least one R¹ selected from D, F, CF₃, and OCF₃.

3. The active layer of claim 1 wherein the L³ comprises a coordinating group selected from alkoxide, carboxylate, thiocarboxylate, dithiocarboxylate, sulfonate, thiolate, carbamate, dithiocarbamate, thiocarbazone anions, sulfonamide anions, halide, nitrate, sulfate, and hexahaloantimonate.

4. The active layer of claim 1 wherein $L^4$ has Formula XIII, $$PAr_3 \qquad (XIII)$$

where Ar is selected from aryl and heteroaryl groups.

5. The active layer of claim 1 wherein substantially 100% by weight of the active layer comprises at least one compound having a formula selected from Formula II.

6. An organic electronic device comprising at least one active layer of claim 1.

7. The device of claim 6 wherein the active layer is a charge transport layer.

8. The device of claim 6, further comprising a hole transport layer comprising a hole transport material selected from N,N'-diphenyl-N,N'-bis(3-methylphenyl)-[1,1'-biphenyl]-4,4-diamine; 1,1-bis[(di-4-tolylamino)phenyl]cyclohexane; N,N'-bis(4-methylphenyl)-N,N'-bis(4-ethylphenyl)-[1,1'-(3,3'-dimethyl)biphenyl]-4,4'-diamine; tetrakis-(3-methylphenyl)-N,N,N',N'-2,5-phenylenediamine; α-phenyl-4-N,N-diphenylaminostyrene; p-(diethylamino)-benzaldehyde diphenylhydrazone; triphenylamine; bis[4-(N,N-diethylamino)-2-methylphenyl](4-methylphenyl)methane; 1-phenyl-3-[p-(diethylamino)styryl]-5-[p-(diethylamino)phenyl]pyrazoline; 1,2-trans-bis(9H-carbazol-9-yl)cyclobutane; N,N,N',N'-tetrakis(4-methylphenyl)-(1,1'-biphenyl)-4,4'-diamine; porphyrinic compounds; and combinations thereof.

9. The active layer of claim 1 wherein the layer further comprises a diluent selected from the group consisting of poly(N-vinyl carbazole); polysilane; 4,4'-N,N'-dicarbazole biphenyl; or tertiary aromatic amines.

* * * * *